(12) United States Patent
Choi et al.

(10) Patent No.: US 12,415,090 B2
(45) Date of Patent: Sep. 16, 2025

(54) LASER IRRADIATION DEVICE

(71) Applicant: Lameditech CO., LTD., Seoul (KR)

(72) Inventors: Jong Seok Choi, Incheon (KR); Bong Kyoon Jeong, Bucheon-si (KR); Myung Su Jang, Seoul (KR); Ju Hun Lee, Anyang-si (KR)

(73) Assignee: Lameditech CO., LTD., Seoul (KR)

( * ) Notice: Subject to any disclaimer, the term of this patent is extended or adjusted under 35 U.S.C. 154(b) by 504 days.

(21) Appl. No.: 17/940,669

(22) Filed: Sep. 8, 2022

(65) Prior Publication Data

US 2023/0381536 A1   Nov. 30, 2023

Related U.S. Application Data

(63) Continuation of application No. PCT/KR2022/012716, filed on Aug. 25, 2022.

(30) Foreign Application Priority Data

May 30, 2022 (KR) .................. 10-2022-0065971

(51) Int. Cl.
*A61N 5/067* (2006.01)
*A61N 1/32* (2006.01)
*A61N 5/06* (2006.01)

(52) U.S. Cl.
CPC ............. *A61N 5/067* (2021.08); *A61N 1/325* (2013.01); *A61N 5/0616* (2013.01); *A61N 2005/0626* (2013.01)

(58) Field of Classification Search
CPC ...... A61N 5/067; A61N 1/325; A61N 5/0616; A61N 2005/0626; A61N 1/08; A61N 1/30;
(Continued)

(56) References Cited

U.S. PATENT DOCUMENTS 7,194,316 B2 *  3/2007  Bousfield ............. A61N 5/0617
                                                           607/139
7,890,164 B2 *  2/2011  Akiyama ................ A61N 1/303
                                                            604/20
(Continued)

FOREIGN PATENT DOCUMENTS

CN         109248384 A  *  1/2019
EP           2314245 A1  *  4/2011  ......... A45D 26/0061
(Continued)

OTHER PUBLICATIONS

CN109248384A Translation (Year: 2019).*
(Continued)

*Primary Examiner* — Niketa Patel
*Assistant Examiner* — Attiya Sayyada Hussaini
(74) *Attorney, Agent, or Firm* — Dinsmore & Shohl LLP; Yongsok Choi, Esq.

(57) ABSTRACT

A laser irradiation device for performing treatment on human skin includes a main body including a barrel part; a laser oscillator that is accommodated in the main body and configured to generate a laser beam to be irradiated through the barrel part; and a skin treatment unit including a lens unit detachably connected to the main body and including a multi-lens that processes the laser beam generated by the laser oscillator into a plurality of laser beams and a functional unit detachably connected to the lens unit.

12 Claims, 13 Drawing Sheets

(58) Field of Classification Search
CPC ... A61N 1/32; A61N 1/36; A61N 5/00; A61N 5/06; A61N 2005/005; A61N 2005/0644; A61N 1/303; A61N 2005/002; A61N 2005/0664; A61B 18/00; A61B 18/20; A61L 2/10
See application file for complete search history.

(56) References Cited

U.S. PATENT DOCUMENTS

| | | | | |
|---|---|---|---|---|
| 2016/0361539 | A1* | 12/2016 | Nathanson | A61N 1/325 |
| 2017/0172659 | A1* | 6/2017 | Choi | A61B 18/203 |
| 2019/0274608 | A1* | 9/2019 | Choi | A61B 5/150748 |

FOREIGN PATENT DOCUMENTS

| | | | | |
|---|---|---|---|---|
| JP | 2015093109 | A | | 5/2015 |
| JP | 2017156643 | A * | | 9/2017 |
| JP | 2019155067 | A | | 9/2019 |
| JP | 2021137536 | A | | 9/2021 |
| KR | 1020050005728 | A | | 1/2005 |
| KR | 200426671 | Y1 | | 9/2006 |
| KR | 101386137 | B1 | | 4/2014 |
| KR | 1020140140394 | A | | 12/2014 |
| KR | 101824460 | B1 | | 2/2018 |
| KR | 101826500 | B1 * | | 2/2018 |
| KR | 1020190106569 | A | | 9/2019 |
| KR | 1020190113308 | A | | 10/2019 |
| KR | 102094456 | B1 * | | 3/2020 |
| KR | 1020210110439 | A | | 9/2021 |

OTHER PUBLICATIONS

KR101826500B1_Translation (Year: 2018).*
KR102094456B1 Translation (Year: 2020).*
JP2017156643A_Translation (Year: 2017).*
Office Action of KR Application No. 10-2022-0065971 dated May 20, 2024.
Office Action of JP Application No. 2022-563382 dated Jul. 16, 2024.

* cited by examiner

LASER IRRADIATION DEVICE

CROSS-REFERENCE TO RELATED APPLICATIONS

This application is a continuation of International Application No. PCT/KR2022/012716 filed on Aug. 25, 2022, which claims priority to Korean Patent Application No. 10-2022-0065971 filed on May 30, 2022, the entire contents of which are herein incorporated by reference.

TECHNICAL FIELD

The present disclosure relates to a laser irradiation device for performing treatment on human skin.

BACKGROUND

Recently, as various medical devices have been developed along with the development of various high technologies, high-tech laser devices are being used more often than ever before in the medical field to treat various diseases.

One of the uses of a medical laser is to perforate skin by irradiating a laser to the skin in order to collect blood from the perforated skin, administer a drug into a perforation, or remove moles or freckles from the skin.

Meanwhile, various treatments using various high-tech medical devices have recently been introduced for the purpose of not only medical treatment for diseases but also skin beauty. For example, there is galvanic or iontophoresis treatment which changes the electrical environment of the skin using the potential difference to increase the permeation of an ionic drug into the skin. Also, ultrasound treatment by which ultrasound is applied to the skin to stimulate skin regeneration or treatment is being used in various ways.

As described above, in the medical and cosmetic fields, the demand for treatments using laser, iontophoresis and ultrasound has been increasing, and devices or methods for effectively providing such treatments are needed.

(Patent Document 1) Korean Patent Laid-open Publication No. 10-2014-0140394 (published on Dec. 9, 2014)

(Patent Document 2) Korean Patent Laid-open Publication No. 10-2005-0005728 (published on Jan. 14, 2005)

SUMMARY

Problems to be Solved by the Invention

The present disclosure is conceived to solve the above-described problems in the prior art and provides a laser irradiation device configured to share a laser treatment unit and thus increase the convenience of each treatment.

The present disclosure also provides a laser irradiation device capable of removing heat generated therein when in operation.

However, problems to be solved by the present disclosure are not limited to the above-described problems. There may be other problems to be solved by the present disclosure.

Means for Solving the Problems

As a means for solving the problems, according to an aspect of the present disclosure, a laser irradiation device for performing treatment on human skin includes a main body including a barrel part; a laser oscillator that is accommodated in the main body and configured to generate a laser beam to be irradiated through the barrel part; and a skin treatment unit including a lens unit detachably connected to the main body and including a multi-lens that processes the laser beam generated by the laser oscillator into a plurality of laser beams and a functional unit detachably connected to the lens unit.

The above-described aspects are provided by way of illustration only and should not be construed as liming the present disclosure. Besides the above-described embodiments, there may be additional embodiments described in the accompanying drawings and the detailed description.

Effects of the Invention

According to any one of the aspects of the present disclosure, various treatments such as iontophoresis treatment in combination with laser treatment can be quickly and conveniently switched and performed. Therefore, the subject's satisfaction and treatment effect can be increased, and the operator's convenience in use can be improved.

Also, the laser irradiation device has a cooling function and thus is capable of removing heat generated therein when in operation. Therefore, the lifespan of internal components of the laser irradiation device can be increased.

DETAILED DESCRIPTION OF THE INVENTION

Hereafter, embodiments of the present disclosure will be described in detail with reference to the accompanying drawings so that the present disclosure may be readily implemented by a person with ordinary skill in the art. However, it is to be noted that the present disclosure is not limited to the embodiments but may be embodied in various other ways. In drawings, parts irrelevant to the description are omitted for the simplicity of explanation, and like reference numerals denote like parts through the whole document.

Through the whole document, the term "comprises or includes" and/or "comprising or including" used in the document means that one or more other components, steps, operation and/or existence or addition of elements are not excluded in addition to the described components, steps, operation and/or elements unless context dictates otherwise. Further, through the whole document, the term "connected to" or "coupled to" that is used to designate a connection or coupling of one element to another element includes both a case that an element is "directly connected or coupled to" another element and a case that an element is "electronically connected or coupled to" another element via still another element. Furthermore, through the whole document, the term "on" that is used to designate a position of one element with respect to another element includes both a case that the one element is adjacent to the other element and a case that any other element exists between these two elements.

Hereinafter, an embodiment of the present disclosure will be described in detail with reference to the accompanying drawings.

Figure 1:
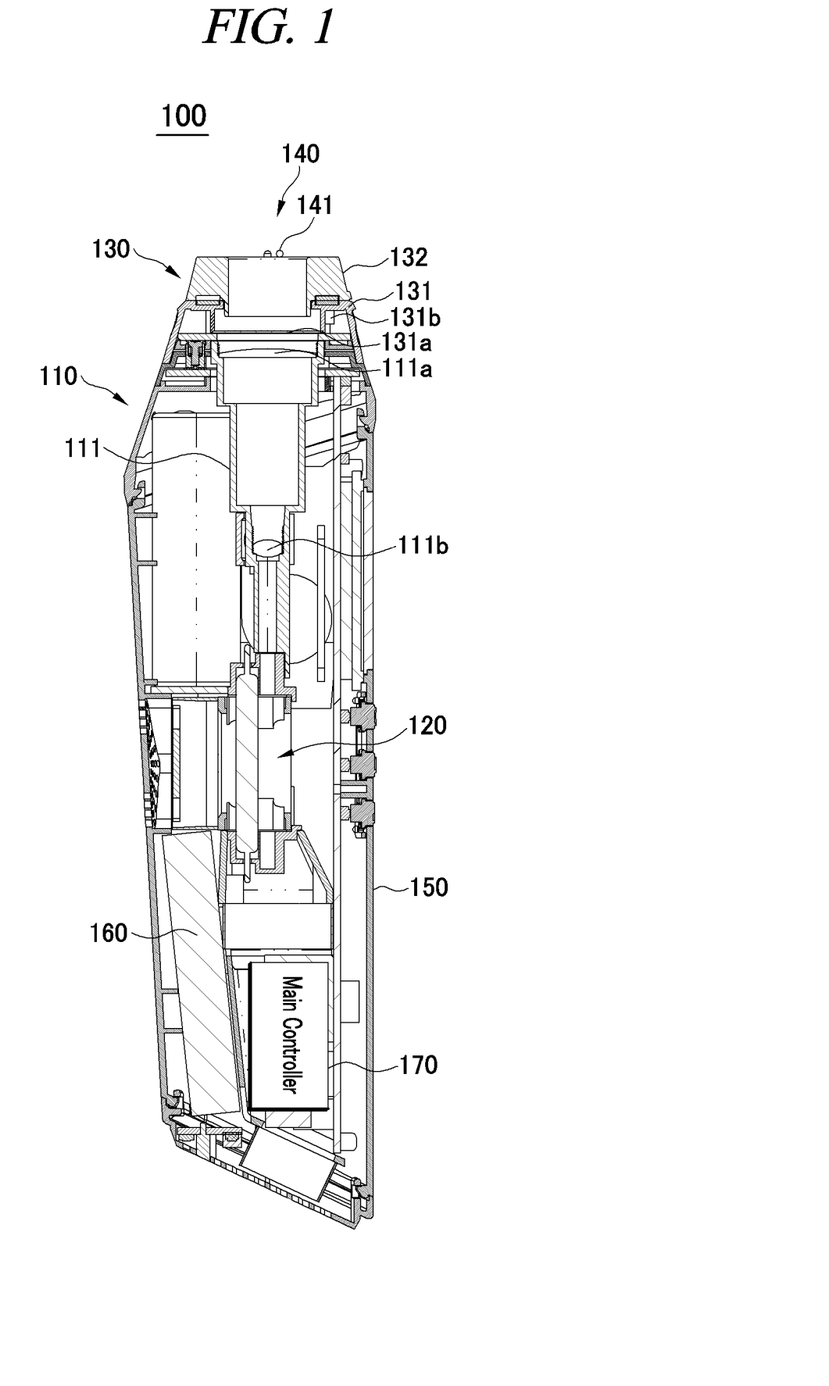
FIG. 1 is a cross-sectional view of a laser irradiation device.
Figure 2A:
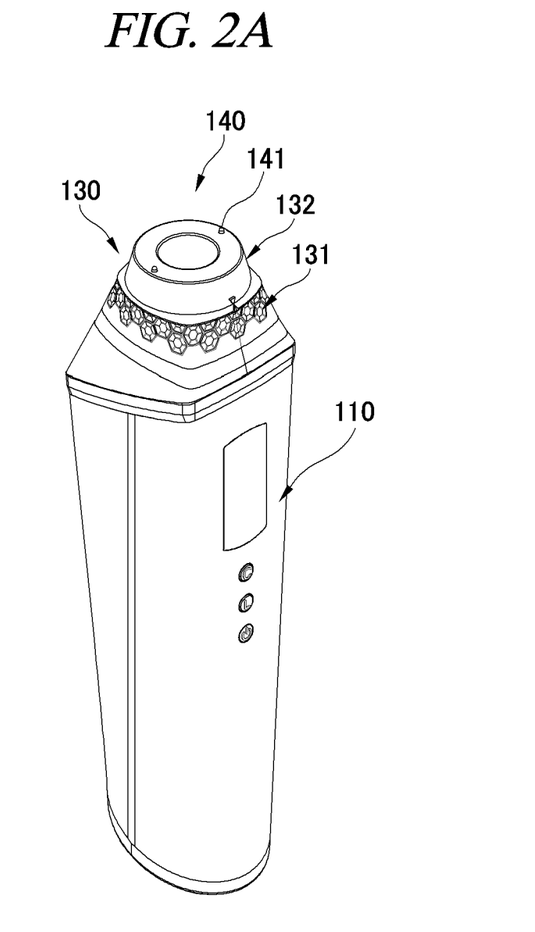
FIG. 2A is a perspective view of the laser irradiation device.
Figure 2B:
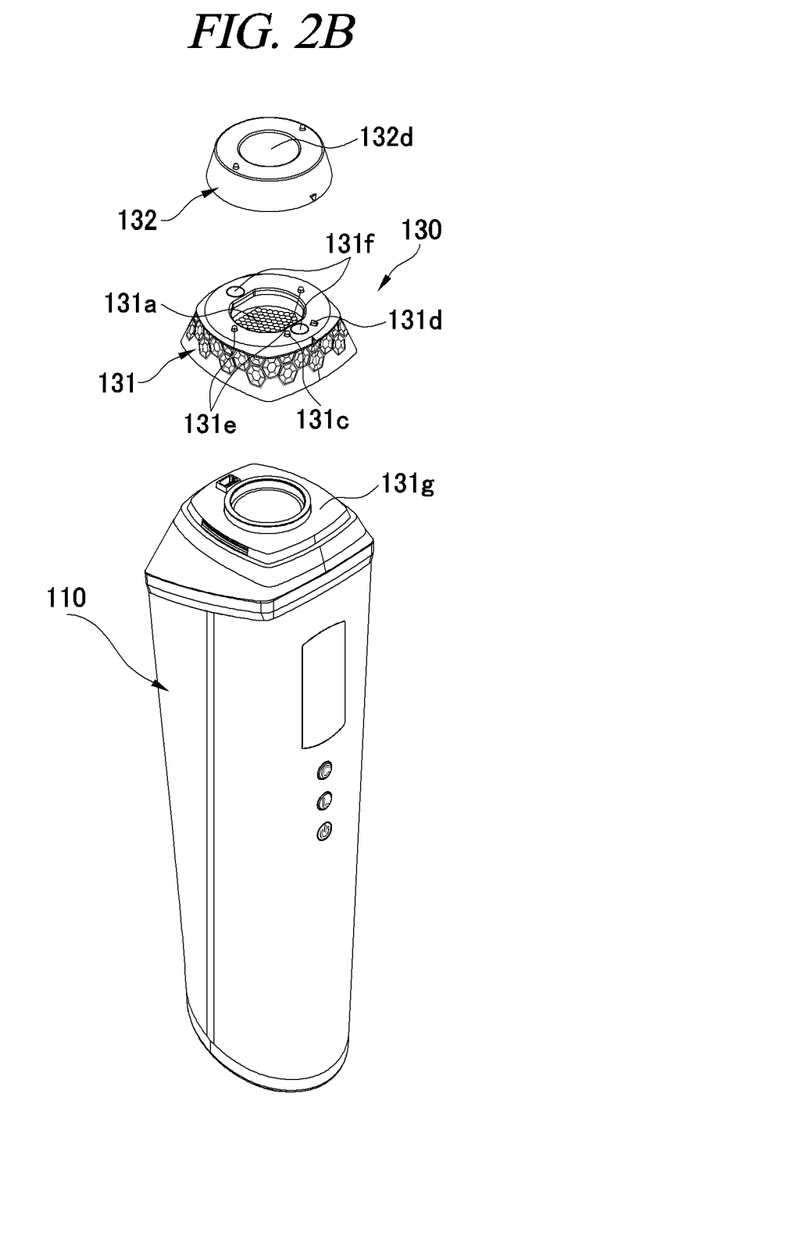
FIG. 2B is a perspective view of the laser irradiation device.

FIG. 1 is a cross-sectional view of a laser irradiation device, and FIG. 2 is a perspective view of the laser irradiation device. Referring to FIG. 1 and FIG. 2, a laser irradiation device 100 for performing treatment on human skin may include a main body 110, a laser oscillator 120, a skin treatment unit 130, a contact sensor unit 140, a grip sensing unit 150, a battery 160 and a main controller 170. However, the laser irradiation device 100 illustrated in FIG. 1 and FIG. 2 is just an embodiment of the present disclosure and can be modified in various ways based on the components shown in FIG. 1 and FIG. 2.

Referring to FIG. 1, the main body 110 forms the exterior of the laser irradiation device 100 and may include a barrel part 111. The barrel part 111 may have a substantially cylindrical shape and its one side may be connected to the laser oscillator 120 and the other side may be connected to the skin treatment unit 130.

A forward lens 111a configured to guide a laser beam forward and a backward lens 111b may be provided in the barrel part 111. Specifically, the forward lens 111a and the backward lens 111b may be provided at predetermined locations inside the barrel part 111 along a longitudinal direction of the barrel part 111. For example, the forward lens 111a may be disposed on the barrel part 111 and the backward lens 111b may be disposed under the barrel part 111.

The forward lens 111a and the backward lens 111b may process a laser beam generated by the laser oscillator 120 and guide the laser beam in the longitudinal direction. In particular, the backward lens 111b may be adjusted in location along the longitudinal direction. For example, the backward lens 111b may be adjusted upwards or downwards along the longitudinal direction of the barrel part 111. The location of the backward lens 111b may be directly adjusted by an operator using an adjusting screw (not shown) provided on a predetermined outside surface of the main body 110.

The number, size and intensity of laser beams may be regulated based on the adjusted location of the backward lens 111b. For example, the backward lens 111b may process the laser beam generated by the laser oscillator 120 by dividing the laser beam into a plurality of laser beams and guide each laser beam to be irradiated in the longitudinal direction of the barrel part 111 (forward) in parallel with each other.

The laser oscillator 120 is accommodated in the main body 110 and generates a laser beam to be irradiated through the barrel part 111. Specifically, the laser oscillator 120 may include a laser charging capacitor. The laser oscillator 120 may be arranged in series side by side with the barrel part 111 so that the generated laser beam is directed toward the barrel part 111.

The skin treatment unit 130 is a component for performing laser treatment or iontophoresis treatment to a subject. In particular, the skin treatment unit 130 is detachably connected to the main body 110, and, thus, the skin treatment unit 130 may perform laser treatment to the skin of the subject and then perform iontophoresis treatment to the laser treated area (irradiation target area) in combination with the laser treatment.

Specifically, after the operator performs the laser treatment to the irradiation target area, the skin treatment unit 130 may be mounted on the main body 110 and then operated to perform the treatment while being in contact with the irradiation target area (contact target area). Here, the skin treatment unit 130 may be electrically connected to a contact sensing unit 141 to transmit an electrical current for iontophoresis treatment to the contact target area.

The skin treatment unit 130 can be detached from and attached to the main body 110 and includes a lens unit 131 and a functional unit 132.

Referring to FIG. 2A and FIG. 2B, the lens unit 131 includes a multi-lens 131a that is detachably connected to the main body 110 and processes a laser beam generated by the laser oscillator 120 into a plurality of laser beams. For example, the multi-lens 131a may be composed of a plurality of lenses that is spaced apart from each other in a longitudinal direction. The multi-lens 131a can divide a laser beam into a plurality of laser beams.

According to a conventional technology, a multi-lens used for a laser irradiation device is located inside the laser irradiation device. Therefore, it is difficult to replace the lens only.

However, the laser irradiation device 100 according to the present disclosure includes the multi-lens 131a in the lens unit 131 that can be detached from and attached to the main body 110 as shown in FIG. 2B. Therefore, if the lens is damaged by long-term use, the multi-lens 131a can be replaced when the lens unit 131 is replaced. Accordingly, it is possible to suppress a decrease in energy efficiency of the laser irradiation device 100 caused by damage to the lens.

Referring to FIG. 2B, the lens unit 131 may include a galvanic electrode 131c, a galvanic sensor 131d, contact sensing units 131e and tip holding magnets 131f on its upper surface.

For example, if the combined functional unit 132 is an iontophoresis module, the functional unit 132 may be in contact with the galvanic electrode 131c and the galvanic sensor 131d may recognize the iontophoresis module.

Also, the lens unit 131 may include a memory unit 131b. When the memory unit 131b receives a laser oscillation signal to generate a laser beam from the laser oscillator 120, the memory unit 131b may manage the replacement period of the lens unit 131 based on the number of laser oscillation signals.

For example, the memory unit 131b may store information of each laser oscillation signal and count the number of laser oscillation signals. For another example, if the lens unit 131 is replaced with a new one, the memory unit 131b may deduct one for each laser oscillation signal from a predetermined count number, e.g., 500. Then, when the counter number becomes 0, the memory unit 131b may transmit information that the lens unit 131 is to be replaced to the main controller 170.

Further, when the number of laser oscillation signals reaches a predetermined threshold value, the memory unit 131*b* may transmit information that the functional unit 132 is to be replaced to the main controller 170. For example, the memory unit 131*b* may store information of each laser oscillation signal and count the number of laser oscillation signals.

The functional unit 132 is detachably connected to the lens unit 131. For example, the functional unit 132 may operate as a laser module or an iontophoresis module.

The functional unit 132 includes the contact sensor unit 140 configured to sense a contact with a contact target area, and a tip 132*d* on its upper surface. A laser beam may be irradiated through the tip 132*d*. Herein, the tip 132*d* may be designed in various shapes, and a laser beam may be irradiated in various forms depending on the shape of the tip 132*d*.

The contact sensor unit 140 includes the contact sensing unit 141 that is formed at an end portion of the main body 110 and senses a contact with a contact target area. For example, the contact sensor unit 140 may sense a contact with the subject's skin based on an electrical signal generated at the time of contact with a contact target area and at the same time, the contact sensor unit 140 may automatically oscillate laser beams at a predetermined time interval.

The contact sensing unit 141 may be located at the end portion of the main body 110 to be exposed to the outside and may be made of a conductive material to allow an electrical current to flow. For example, the contact sensing unit 141 may be composed of a plurality of pins whose one ends are exposed to the outside.

The contact sensor unit 140 may be connected to the contact sensing unit 141 and configured to sense an electrical current flowing through the contact sensing unit 141. When the skin treatment unit 130 is in close contact with the skin around the irradiation target area of the subject, the contact sensor unit 140 senses an electrical current flowing through the contact sensing unit 141. Thus, the contact sensor unit 140 may serve as a safety device that determines whether to allow the laser irradiation device 100 to irradiate a laser beam.

The grip sensing unit 150 may be formed on a surface of the main body 110 to sense whether the operator is gripping the main body 110. For example, the grip sensing unit 150 may be configured to sense a change in an optical signal or an electrical current signal caused by the operator's touch.

Specifically, if the operator grips the main body 110 while forming a predetermined electrical pattern on the surface of the main body 110, the grip sensing unit 150 may sense the operator's grip by measuring a change in resistance.

When the condition in which the grip sensing unit 150 senses the operator's grip is satisfied, the operation of the skin treatment unit 130 may be allowed, and main controller 170 to be described later may determine whether or not the condition is satisfied.

The battery 160 may be provided inside the main body 110 and may be configured to supply power to operate the laser oscillator 120 and supply power to the skin treatment unit 130. For example, the battery 160 may be located inside the main body 110 and may be charged with power supplied from the outside.

The main controller 170 may be located inside the main body 110. The main controller 170 may be activated in a laser irradiation mode or an iontophoresis mode to control the operation of the laser oscillator 120. For example, the main controller 170 may transmit an operation-related signal to the laser module or the iontophoresis module through the contact sensor unit 140.

Specifically, when the grip sensing unit 150 senses the operator's grip and the contact sensor unit 140 senses a contact between the operator and the contact sensing unit 141, the main controller 170 may control a laser beam to be irradiated in response to an input of a shot button 171 of an interface unit (not shown).

The interface unit is a component for the operator to operate the laser irradiation device 100 and check the status thereof. The interface unit may be configured to receive a signal for manipulating the main controller 170. For example, a laser irradiation signal may be input through the shot button, and a signal for irradiating a laser beam or operating the skin treatment unit 130 may be input through a mode setting button. Further, a status display lamp may visually provide mode setting and detailed information of the laser irradiation device 100.

Specifically, when the functional unit 132 is combined with the main body 110, the main controller 170 may control the functional unit 132 to operate in any one of a laser mode in which an electrical current of a first polarity is transmitted to the contact target area and an iontophoresis mode in which an electrical current of a second polarity different from the first polarity is transmitted to the contact target area.

When the functional unit 132 is attached to the main body 110 and serves as a laser module, the main controller 170 operates the functional unit 132 in the laser mode, and when the functional unit 132 is attached to the main body 110 and serves as an iontophoresis module, the main controller 170 operates the functional unit 132 in the iontophoresis mode.

As described above, the laser irradiation device 100 includes the skin treatment unit 130 that is mounted on the main body 110 and performs laser treatment or iontophoresis treatment. Accordingly, iontophoresis treatment in combination with laser treatment can be performed conveniently without any equipment replacement or location movement. Since the combination of treatments is performed conveniently, the subject's satisfaction and treatment effect can be increased and the operator can efficiently perform a complex procedure.

Hereinafter, a detailed configuration and function of the skin treatment unit 130 of the present disclosure will be described with reference to FIG. 3 and FIG. 4.

FIG. 3 and FIG. 4 are diagrams for explaining functional units. FIG. 3 is a perspective view of the functional unit 132. The functional unit 132 may include a laser module for laser treatment to the contact target area or an iontophoresis module that generates and controls an electrical current for iontophoresis treatment to the contact target area.

Figure 3A:
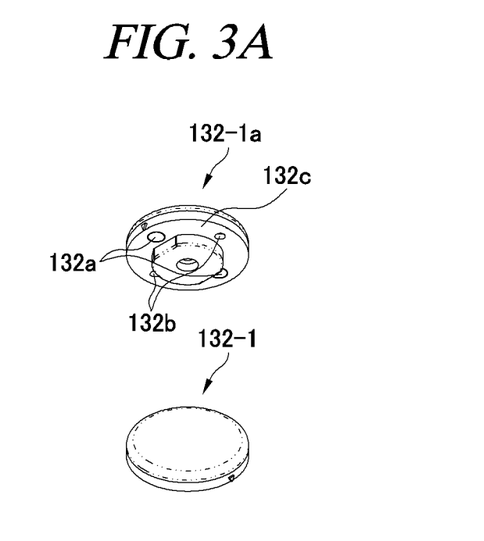
FIG. 3A is diagram for explaining functional units.

A functional unit 132-1 shown in FIG. 3A is an iontophoresis module, and may include tip holding magnets 132*a*, contact sensing unit contact surfaces 132*b* and a contact surface 132*c* on its lower surface 132-1*a*.

The functional unit 132-1 shown in FIG. 3A may be in contact with the galvanic electrode 131*c* of the lens unit 131 through the contact surface 132*c* on the lower surface 132-1*a*, and may enable treatment to be performed in a galvanic mode.

Figure 3B:
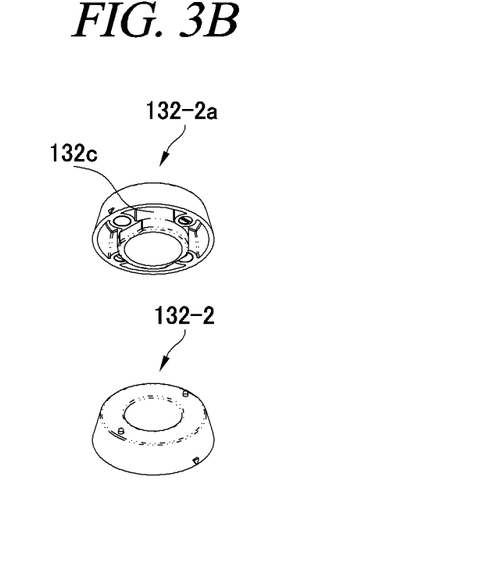
FIG. 3B is diagram for explaining functional units.
Figure 3C:
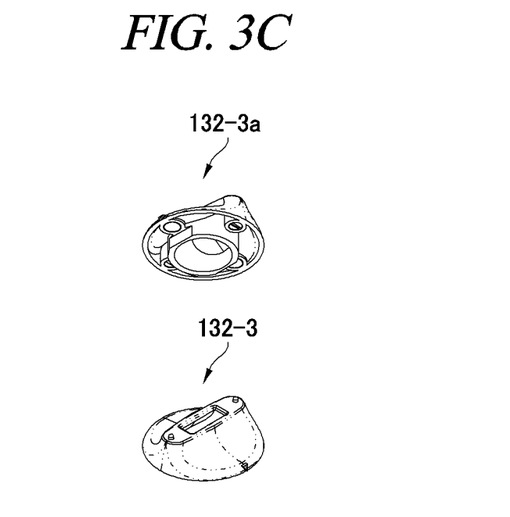
FIG. 3C is diagram for explaining functional units.
Figure 3D:
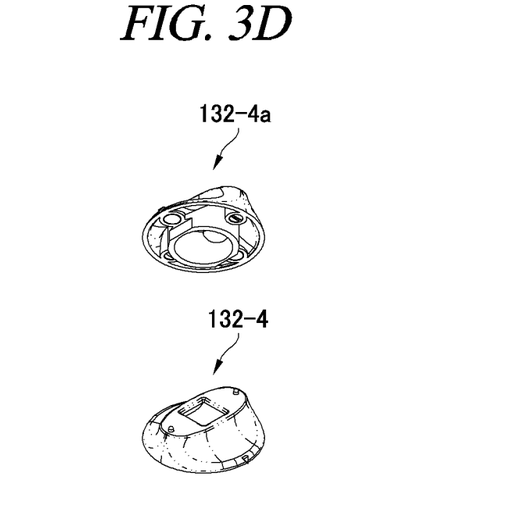
FIG. 3D is diagram for explaining functional units.
Figure 4A:
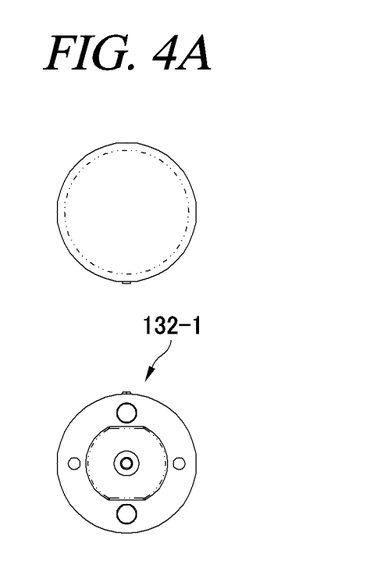
FIG. 4A is diagram for explaining functional units.
Figure 4B:
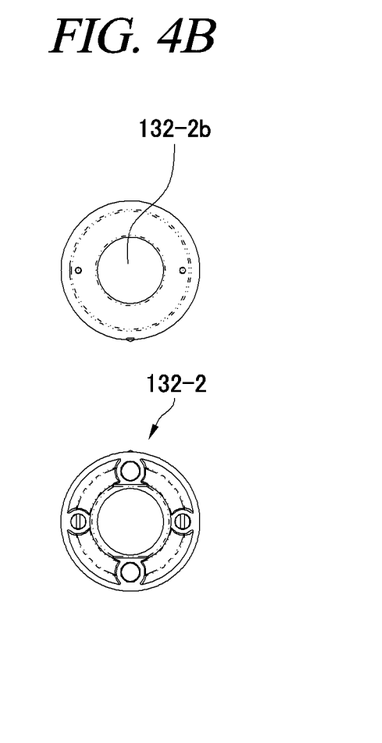
FIG. 4B is diagram for explaining functional units.
Figure 4C:
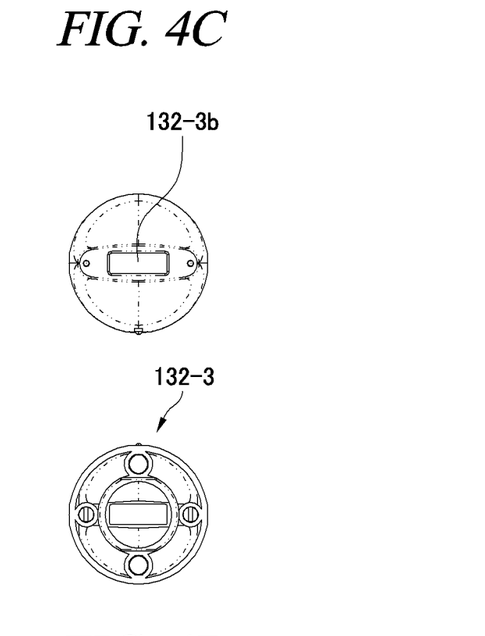
FIG. 4C is diagram for explaining functional units.
Figure 4D:
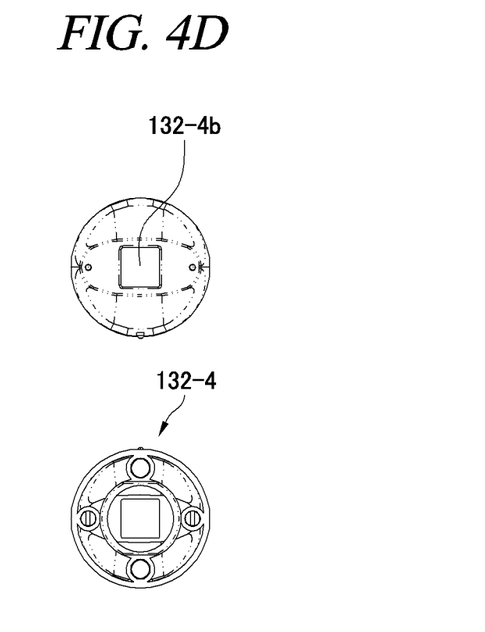
FIG. 4D is diagram for explaining functional units.

Functional units 132-2, 132-3 and 132-4 shown in FIG. 3B to FIG. 3D are laser modules, and may include the tip holding magnets 132*a* and the contact sensing unit contact surfaces 132*b* on their lower surfaces 132-2*a*, 132-3*a* and 132-4*a*. The contact surfaces 132*c* may be hollow spaces.

The functional units 132-2, 132-3 and 132-4 shown in FIG. 3B to FIG. 3D have hollow spaces as the contact surfaces 132*c* in their lower surfaces 132-2*a*, 132-3*a* and 132-4*a* and thus cannot be in contact with the galvanic electrode 131c of the lens unit 131. Therefore, the functional units 132-2, 132-3 and 132-4 may enable treatment to be performed in the laser mode.

FIG. 4 is a plan view of the functional unit 132. The functional unit 132-1 shown in FIG. 4A is an iontophoresis module, and the functional units 132-2, 132-3 and 132-4 shown in FIG. 4B to FIG. 4D are laser modules. The functional unit 132-2 shown in FIG. 4B has a circular tip 132-2b, the functional unit 132-3 shown in FIG. 4C has a rectangular tip 132-3b, and the functional unit 132-4 shown in FIG. 4D has a square tip 132-4b. The tip of the functional unit 132 may be designed in various shapes, and is not limited to the present embodiment.

Figure 5A:
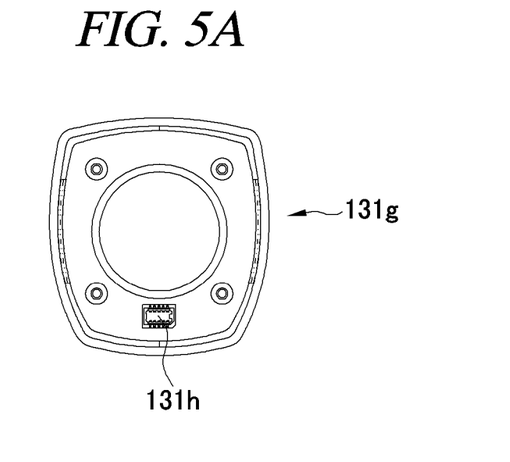
FIG. 5A is a diagram for explaining a lens unit.
Figure 5B:
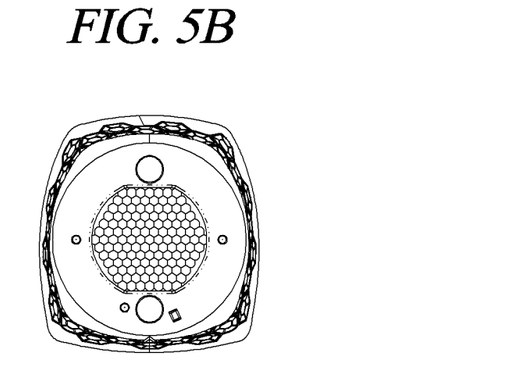
FIG. 5B is a diagram for explaining a lens unit.

FIG. 5 is a diagram for explaining coupling of a lens unit. Referring to FIG. 2, the main body 110 has a lens unit contact surface 131g to be in contact with the lens unit 131. FIG. 5A illustrates the lens unit contact surface 131g, and FIG. 5B illustrates a lower part of the lens unit contact surface 131g.

Referring to FIG. 5A, the lens unit contact surface 131g may include a communication connector 131h. For example, the communication connector 131h may be an EEP-ROM or a touch sensor. Referring to FIG. 2 and FIG. 5, when the lens unit 131 is attached to the lens unit contact surface 131g of the main body 110, the laser irradiation device 100 may recognize the attachment of the lens unit 131 through the communication connector 131h.

Figure 6:
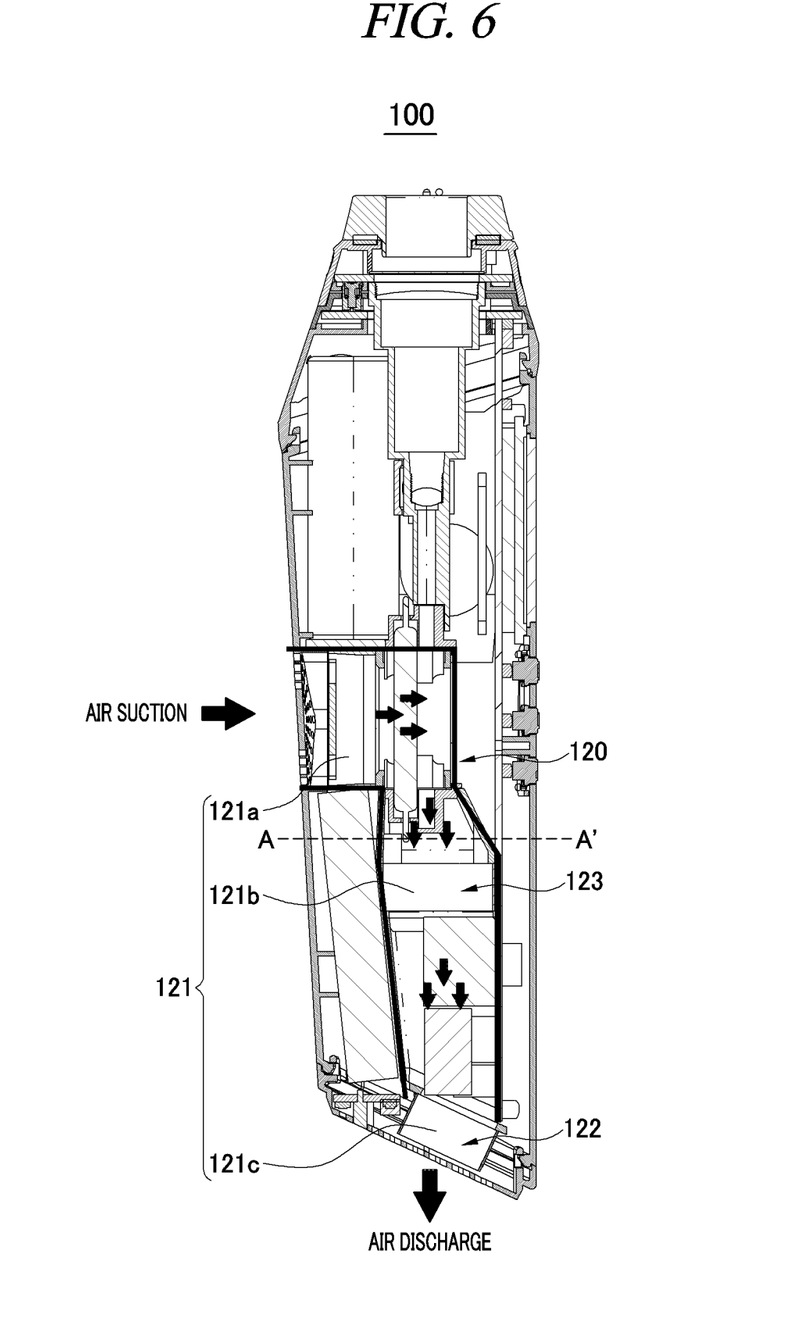
FIG. 6 is a diagram for explaining air circulation in a laser oscillator.
Figure 7:
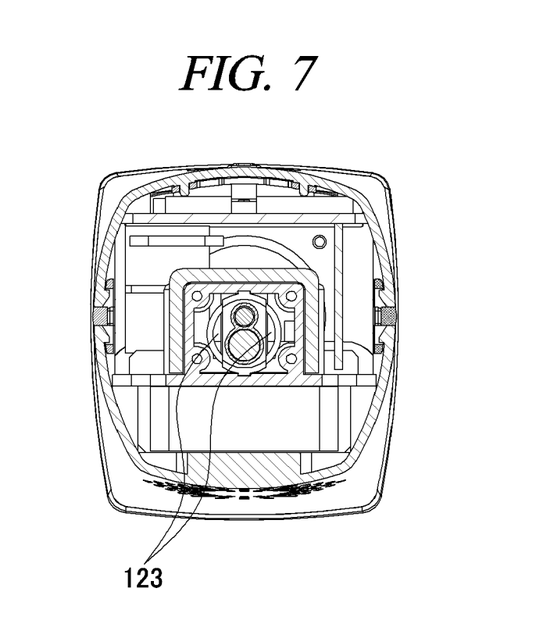
FIG. 7 is a cross-sectional view of the laser oscillator as taken along line A-A' of FIG. 6.

FIG. 6 is a diagram for explaining air circulation in a laser oscillator, and FIG. 7 is a cross-sectional view of the laser oscillator as taken along line A-A' of FIG. 6. The laser irradiation device 100 itself has a cooling function and can remove heat generated in the laser oscillator 120 when in operation.

Referring to FIG. 6, the laser irradiation device 100 may further include a fan 121 and at least one ventilation hole 123. The fan 121 may introduce external air into the laser oscillator 120.

Herein, the fan 121 may be composed of a first fan 121a, a second fan 121b and a third fan 121c and may form a flow of air. For example, the first fan 121a may be located to be connected to the main body 110 and configured to suck external air into the laser oscillator 120. The second fan 121b is located between the laser oscillator 120 and an exhaust unit 122 to form a flow of the external air sucked by the first fan 121a toward the exhaust unit 122. Then, the third fan 121c may discharge the sucked-in external air to the outside through the exhaust unit 122.

Referring to FIG. 7, the ventilation holes 123 are formed on one side of the laser oscillator 120 and may discharge external air toward the exhaust unit 122. For example, the ventilation holes 123 may be formed on both sides of the laser oscillator 120. External air sucked by the first fan 121a may be supplied into the laser oscillator 120 through the ventilation holes 123, and, thus, heat generated therein may be removed by air cooling.

As described above, the laser irradiation device 100 may remove internal heat generated when the laser oscillator 120 oscillates laser beams by discharging the internal heat to the outside. Therefore, it is possible to more effectively perform laser treatment with the laser irradiation device 100 and also possible to increase the lifespan of internal components of the laser irradiation device 100.

Figure 8A:
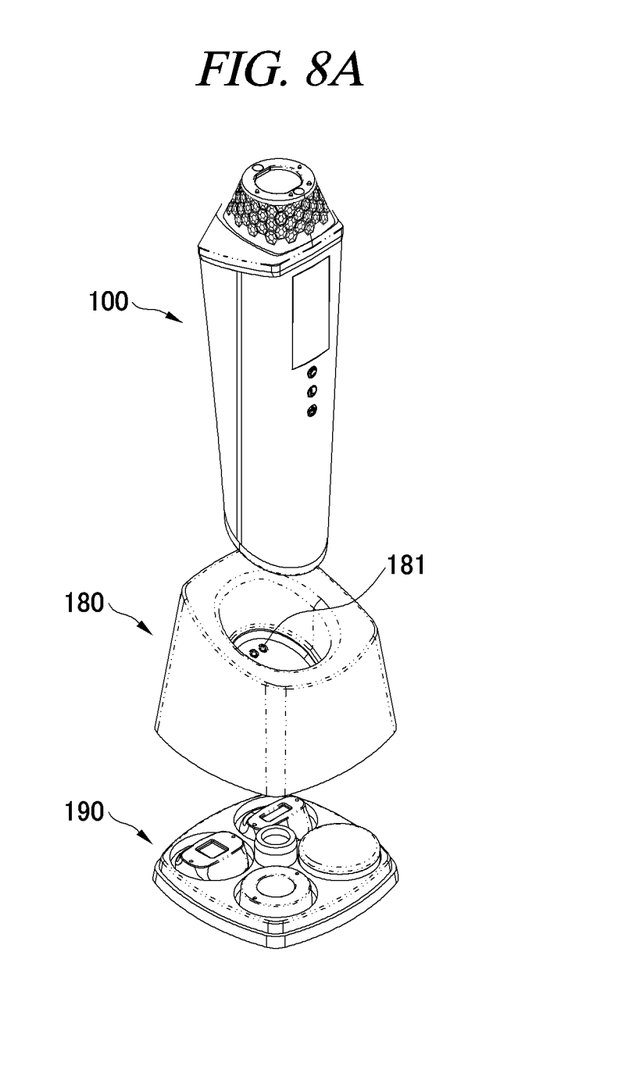
FIG. 8A is a diagram for explaining a charging stand.
Figure 8B:
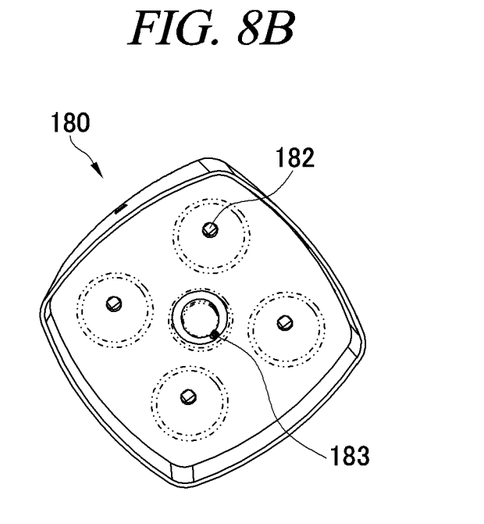
FIG. 8B is a diagram for explaining a charging stand.

FIG. 8 is a diagram for explaining a charging stand. Referring to FIG. 8A, the laser irradiation device 100 may include a charging stand 180 and a tip stand 190. For example, the laser irradiation device 100 may be inserted into the charging stand 180 and the battery may be charged.

As shown in FIG. 8A, the charging stand 180 includes a groove in the middle, and the laser irradiation device 100 may be inserted and fixed through the groove. The charging stand 180 may include charging terminals 181 in an upper surface of the groove where the laser irradiation device 100 is to be inserted.

For example, the laser irradiation device 100 may be inserted into the groove of the charging stand 180 and brought into contact with the charging terminals 181, and, thus, the battery 160 provided therein may be charged.

The laser irradiation device 100 inserted into the charging stand 180 may also be inserted into the tip stand 190. The laser irradiation device 100 may sterilize the tip 132d of the functional unit 132 through the tip stand 190 while the battery 160 is charged.

Figure 9A:
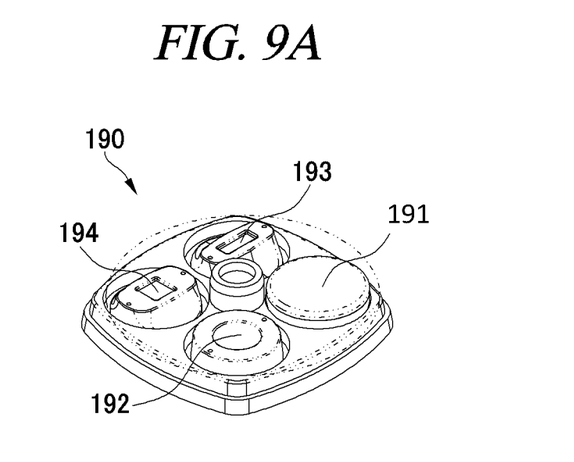
FIG. 9A is a diagram for explaining a tip stand.
Figure 9B:
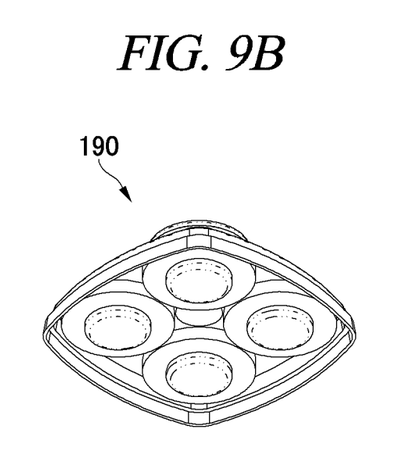
FIG. 9B is a diagram for explaining a tip stand.

The tip stand 190 is configured to retain the functional unit 132 of the skin treatment unit 130 that can be detached from and attached to the main body 110, and may be coupled to a lower part of the charging stand 180. FIG. 9 is a diagram for explaining the tip stand 190. FIG. 9A illustrates an upper surface of the tip stand 190, and FIG. 9B illustrates a lower surface of the tip stand 190. The tip stand 190 may include a plurality of grooves to accommodate the functional unit 132. For example, the functional unit 132 may be accommodated and retained in the grooves of the tip stand 190.

For example, referring to FIG. 9A, the tip stand 190 may retain at least one of a functional unit 191 including an iontophoresis module detached from the lens unit 131, a functional unit 192 having a circular tip, a functional unit 193 having a rectangular tip and a functional unit 194 having a square tip. The functional units 191 to 194 retained in the tip stand 190 may be coupled to the charging stand 180 and sterilized.

Referring back to FIG. 8B, the charging stand 180 may include a plurality of UV LEDs 182 and a UV safety unit 183 on its lower surface. The plurality of UV LEDs 182 may sterilize the functional units retained in the tip stand 190, and the UV safety unit 183 may control the operation of the UV LEDs 182.

Specifically, referring to FIG. 8 and FIG. 9, the tip stand 190 where the functional units 191 to 194 are retained may be coupled to the charging stand 180. The lower surface of the charging stand 180 may be coupled to the upper surface of the tip stand 190.

After the coupling, the functional units 191 to 194 retained in the tip stand 190 may be sterilized by the plurality of UV LEDs 182 provided on the lower surface of the charging stand 180.

When the charging stand 180 is separated from the tip stand 190, the UV LEDs 182 may stop the sterilization. For example, the UV safety unit 183 may sense whether the lower surface of the charging stand 180 is coupled to the tip stand 190 and is in a closed state. The UV safety unit 183 may control the UV LEDs 182 to operate only when the lower surface of the charging stand 180 is coupled to the tip stand 190 and is in a closed state.

Alternatively, when charging of the battery of the laser irradiation device 100 is stopped in the charging stand 180, sterilization by the UV LEDs 182 may also be stopped. For example, when the laser irradiation device 100 is separated from the charging stand 180 coupled to the tip stand 190, i.e., when charging of the battery is stopped, sterilization by the UV LEDs 182 may also be stopped.

As described above, the laser irradiation device 100 can be kept clean by sterilizing the tip 132d of the functional unit 132 while charging the internal battery. The laser irradiation device 100 sterilizes the tip 132d by coupling between the charging stand 180 and the tip stand 190 where the functional unit 132 is retained. Thus, it is possible to easily and efficiently manage the functional unit 132.

The above description of the present disclosure is provided for the purpose of illustration, and it would be understood by a person with ordinary skill in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

What is claimed is:

1. A laser irradiation device for performing treatment on human skin, comprising:
   a main body including a barrel part;
   a laser oscillator that is accommodated in the main body and configured to generate a laser beam to be irradiated through the barrel part; and
   a skin treatment unit that is detachably connected to the main body and includes a lens unit including a multi-lens that processes the laser beam generated by the laser oscillator into a plurality of laser beams and a functional unit detachably connected to the lens unit,
   wherein the lens unit further includes:
   a memory unit configured to manage a replacement period of the lens unit based on the number of laser oscillation signals when the memory unit receives a laser oscillation signal to generate a laser beam from the laser oscillator.

2. The laser irradiation device of claim 1, further comprising:
   a contact sensor unit including a contact sensing unit that is formed at an end portion of the main body and configured to sense a contact with a contact target area.

3. The laser irradiation device of claim 1, further comprising:
   a fan configured to introduce external air into the laser oscillator; and
   at least one ventilation hole formed on one side of the laser oscillator and configured to discharge the external air toward an exhaust unit.

4. The laser irradiation device of claim 1,
   wherein the functional unit includes a laser module for laser treatment to a contact target area or an iontophoresis module that generates and controls an electrical current for iontophoresis treatment to the contact target area.

5. The laser irradiation device of claim 4, further comprising:
   a main controller that is located inside the main body and configured to control the functional unit to operate in any one of a laser mode in which a laser is transmitted to a contact target area and an iontophoresis mode in which an electrical current of a first polarity and a second polarity different from the first polarity is transmitted to a contact target area when the functional unit is coupled to the main body.

6. The laser irradiation device of claim 5,
   wherein the main controller operates the functional unit in the laser mode when the functional unit is attached to the main body as a laser module, and
   the main controller operates the functional unit in the iontophoresis mode when the functional unit is attached to the main body as an iontophoresis module.

7. The laser irradiation device of claim 5, further comprising:
   an interface unit configured to receive a signal for manipulating the main controller.

8. The laser irradiation device of claim 1, further comprising:
   a grip sensing unit formed on a surface of the main body to sense whether an operator is gripping the main body.

9. The laser irradiation device of claim 1, further comprising:
   a battery provided inside the main body and configured to supply power to operate the laser oscillator and supply power to the skin treatment unit.

10. The laser irradiation device of claim 1, further comprising:
    a forward lens and a backward lens that are provided at predetermined locations inside the barrel part along a longitudinal direction of the barrel part and configured to process the laser beam generated by the laser oscillator and guide the laser beam in the longitudinal direction,
    wherein the backward lens is adjusted in location along the longitudinal direction.

11. The laser irradiation device of claim 10,
    wherein the number, size and intensity of laser beams are regulated based on the adjusted location of the backward lens.

12. The laser irradiation device of claim 1,
    wherein the memory unit transmits information that the functional unit is to be replaced to a main controller when the number of laser oscillation signals reaches a predetermined threshold value.

* * * * *